United States Patent [19]

Collins et al.

[11] Patent Number: 5,079,948
[45] Date of Patent: Jan. 14, 1992

[54] METHOD FOR CONDUCTING CAPILLARY PRESSURE DRAINAGE AND IMBIBITION ON A CORE SAMPLE OF A POROUS ROCK

[75] Inventors: Samuel H. Collins, DeSoto; R. Michael Davis, North Richland Hills; Ben F. Marek, Coppell, all of Tex.

[73] Assignee: Mobil Oil Corporation, Fairfax, Va.

[21] Appl. No.: 646,295

[22] Filed: Jan. 28, 1991

[51] Int. Cl.$^5$ .............................................. E21B 49/02
[52] U.S. Cl. ............................................ 73/153; 73/38
[58] Field of Search ................ 73/153, 38, 64.3, 64.4; 324/376

[56] References Cited

U.S. PATENT DOCUMENTS

| | | | |
|---|---|---|---|
| 4,381,665 | 5/1983 | Levine et al. | 73/153 X |
| 4,868,751 | 9/1989 | Dogru et al. | 364/422 |
| 4,907,448 | 3/1990 | Givens | 73/153 |
| 4,924,187 | 5/1990 | Sprunt et al. | 324/376 |
| 4,926,128 | 5/1990 | Givens | 324/376 |

OTHER PUBLICATIONS

"Physical Principles of Oil Production", pp. 304–311.

*Primary Examiner*—Jerry W. Myracle
*Attorney, Agent, or Firm*—Alexander J. McKillop; Charles J. Speciale; George W. Hager, Jr.

[57] ABSTRACT

A water-saturated core sample of a porous rock is placed in a sleeve which a hydrophobic membrane in one end and a hydrophilic membrane in a second end. A pressurized hydrocarbon is injected into the core sample through the hydrophobic membrane to displace the water in the core sample whereby it drains through the hydrophilic membrane into a collector. Upon a depressurization of the injected hydrocarbon below the displacement pressure of the hydrophilic membrane, the water imbibes back into the core sample through the hydrophilic membrane. Upon a pressurization of the imbibing water above atmospheric pressure the water displaces the hydrocarbon from the core sample through the hydrophobic membrane.

9 Claims, 1 Drawing Sheet

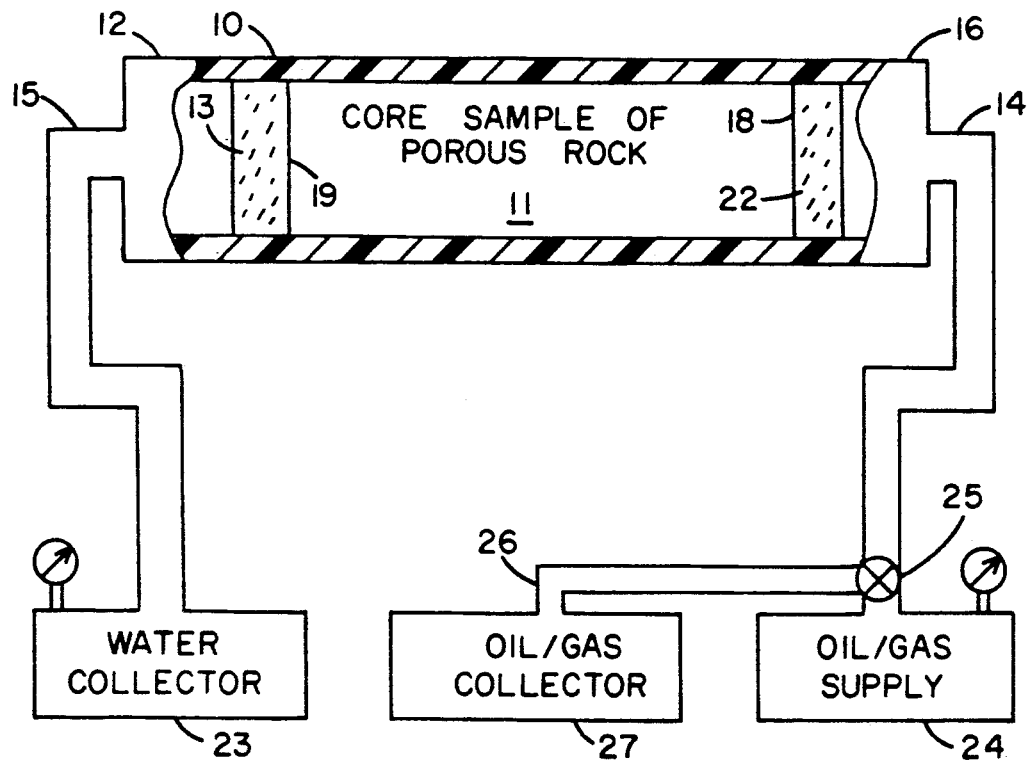

METHOD FOR CONDUCTING CAPILLARY PRESSURE DRAINAGE AND IMBIBITION ON A CORE SAMPLE OF A POROUS ROCK

BACKGROUND OF THE INVENTION

In the drilling of oil wells such as oil and gas wells, cores are taken of the subterranean formation through which the wells are drilled and various characteristics of the cores, or core samples, are determined for the purpose of identifying different fluids in the formation, estimating the quantity of each fluid in the formation, the ease of flow through the formation, etc. Such core samples are also taken from producing reservoirs and characteristics of the core samples are determined for the purpose of estimating particular fluid quantities, predicting production rates, etc.

Two of such characteristics are the capillary pressure drainage and imbibition of a core sample. Such capillary characteristics, as well as measurements thereof, are set forth in *Physical Principles of Oil Production*, McGraw Hill Book Company, 1949, pp 304–311, by Morris Muskat. The importance of determining capillary characteristics pertains to the fluid distribution in a hydrocarbon-bearing (i.e., oil or gas) formation prior to its production. Capillary pressure is the pressure required to cause a fluid to displace from the openings in a porous rock another fluid with which it is not miscible and is dependent on the size of the openings, the interfacial tension between the two fluids, and the contact angle of the system.

Characteristic measurements on a core sample of a porous rock during capillary pressure drainage have been described in U.S. Pat. Nos. 4,907,448 and 4,926,128 to Givens and U.S. Pat. No. 4,924,187 to Sprunt et al. While centrifuge techniques have been used for measurements taken during capillary pressure imbibition, corrections must be applied to such centrifuge measurements for the pressure gradient within the core sample. On the other hand, the measurements taken during capillary pressure drainage described in the aforementioned patents provides a direct measurement of capillary pressure curves (i.e., water saturation versus capillary pressure).

It is a specific object of the present invention to provide a method for conducting capillary pressure drainage and imbibition of a core sample of a porous rock that provides for direct measurement of both capillary drainage and imbibition pressure curves without the limitations of centrifuge techniques on the imbibition measurements.

SUMMARY OF THE INVENTION

In accordance with the present invention, there is provided a method for conducting capillary pressure drainage and imbibition on a core sample of a porous rock from a subterranean formation.

The core sample is initially saturated with a first fluid. A capillary pressure drainage cycle is carried out by injecting a second fluid, under pressure, through a first membrane into the core sample to displace the first fluid through a second membrane. The first membrane is impermeable to the saturating first fluid and is permeable to the displacing second fluid, while the second membrane is permeable to the saturating first fluid and impermeable to the displacing second fluid. A plurality of such capillary pressure drainage cycles are carried out by successively increasing pressure on the displacing second fluid. A first plurality of capillary pressure imbibition cycles are then carried out by successively reducing the pressure on the displacing second fluid below the displacement pressure of the second membrane to allow the displaced, saturating first fluid to imbibe back into the core sample through the second membrane. A second plurality of capillary pressure imbibition cycles are carried out by successively increasing pressure on the displaced saturating first fluid above atmospheric pressure as it imbibes back into the core sample through the second membrane to displace the second fluid from the core sample through the first membrane.

In a more specific aspect, the first fluid is water, preferably brine, and the second fluid is a hydrocarbon, oil or gas. The first membrane is hydrophobic and the second membrane is hydrophilic.

In a yet further aspect, measurements of capillary pressure versus saturation are made for each capillary pressure drainage and imbibition cycle. Also, electrical resistivity measurements may be made for each such drainage and imbibition cycle.

BRIEF DESCRIPTION OF THE DRAWING

The drawing illustrates apparatus for use in the method of the present invention for carrying out capillary pressure drainage and imbibition on a core sample of a porous rock.

DESCRIPTION OF THE PREFERRED EMBODIMENT

Referring to the drawing, a pressure sleeve 10, preferably natural or synthetic rubber, surrounds a cylindrical core sample 11 of a porous rock which is to be investigated as to its capillary pressure drainage and imbibition characteristics. Positioned between the core sample 11 and end 12 of the pressure sleeve 10 is a semi-permeable membrane 13 which is permeable to a first fluid initially saturating the core sample, but is impermeable to a second fluid used to displace the first fluid from the core sample. Positioned between the core sample 11 and end 16 of the pressure sleeve 10 is a semi-permeable membrane 22 which is impermeable to the initial saturating fluid, but is permeable to the displacing fluid.

More particularly, the core sample 11 is initially saturated with an electrically conducting fluid, such as salt water, preferably brine, and placed within sleeve 10 under a confining pressure. Membrane 13 is hydrophilic, that is, water permeable. Consequently, the brine within the core sample is the wetting agent for the membrane 13. Membrane 22 is hydrophobic, that is, not water permeable. Instead, it is permeable to a displacing fluid such as a hydrocarbon (i.e., oil or gas) contained in the pressurized supply vessel 24.

The method of the present invention comprises a plurality of capillary pressure drainage cycles followed by a plurality of capillary pressure imbibition cycles. During the initial capillary pressure drainage cycle, the valve 25 is opened to permit the pressurized hydrocarbon fluid in vessel 24 to pass through a conduit 14 and the hydrophobic membrane 22 into end 18 of the core sample 11 wherein it displaces the initial saturating brine from the end 19 of core sample 11 through the hydrophilic membrane 13 for drainage through conduit 15 into the water collector 23. The pressure on the displacing hydrocarbon fluid is thereafter increased stepwise with fluid equilibrium being established within the core sample between each subsequent step, or drainage cycle. Equilibrium is determined by monitoring the level of the brine collected in the vessel 23 and identifying when such level has remained constant for a fixed period of time, such as 48 hours for example. Characteristic capillary pressure versus saturation measurements, as well as electrical resistivity measurements, may be carried out for each such drainage cycle.

When the core sample has reached a state of fluid equilibrium at a pressure just below the displacement pressure of the hydrophilic membrane 13, the initial capillary pressure imbibition cycle is begun by again reducing stepwise the pressure on the displacing hydrocarbon to allow the displaced brine in collector 23 to imbibe back into the core sample 11 through conduit 15 and hydrophilic membrane 13 during each subsequent step, or imbibition cycle. Again the core sample is allowed to equilibrate at each pressure to permit capillary and/or electrical resistivity measurements. Again, equilibrium is determined by monitoring the level of the brine remaining in vessel 24 and identifying when such level has remained constant for a fixed period of time. When the pressure in the displacing hydrocarbon is at atmospheric pressure, the pressure on the brine in collector 23 is increased stepwise and the hydrocarbon is displaced from the core sample through the hydrophobic membrane 22 and drains through conduits 14 and 26 under the control of valve 25 into a hydrocarbon collector 27. This time equilibrium is determined by monitoring the level of hydrocarbon collected in vessel 27 and identifying when such level has remained constant for a fixed period of time. Characteristic capillary pressure versus saturation measurements, as well as electrical resistivity measurements, may be carried out for each such imbibition cycle.

While the foregoing has described a preferred embodiment of the method of the present invention for carrying out capillary characteristic measurements on a core sample of a porous rock, it is to be understood that various modifications or changes may be made without departing from the spirit and scope of the invention as set forth in the appended claims.

We claim:

1. A method for conducting capillary pressure drainage and imbibition on a core sample of porous rock, comprising „ the steps of:
    a) saturating a core sample of a porous rock with a first fluid,
    b) initiating a first capillary pressure drainage cycle by injecting a pressurized second fluid, immiscible with said first fluid, into said core sample through a first membrane that is permeable to said second fluid and impermeable to said first fluid to cause said first fluid to be displaced from said core sample through a second membrane that is permeable to said first fluid and impermeable to said second fluid,
    c) collecting said first fluid as it is displaced from said core sample,
    d) increasing pressure on said second fluid stepwise and repeating steps (b) and (c) for a plurality of additional capillary pressure drainage cycles with fluid equilibrium being established within the core sample between each capillary pressure drainage cycle,
    e) identifying when the core sample has reached a state of fluid equilibrium at a pressure below the displacement pressure of the second membrane,
    f) initiating a first plurality of capillary pressure imbibition cycles by reducing the pressure on the first fluid stepwise to allow the displaced first fluid to imbibe back into the core sample with fluid equilibrium being established within the core sample between each capillary pressure imbibition cycle,
    g) identifying when the core sample has reached a state of fluid equilibrium at atmospheric pressure on the second fluid, and
    h) initiating a second plurality of capillary pressure imbibition cycles by increasing pressure on the first fluid stepwise to allow the second fluid to be displaced from the core sample through said first membrane.

2. The method of claim 1 further comprising the step of measuring capillary pressure versus saturation for each capillary pressure drainage and imbibition cycle.

3. The method of claim 1 further comprising the step of measuring electrical resistivity for each capillary pressure drainage and imbibition cycle.

4. The method of claim 1 wherein said first fluid is water and said second fluid is a hydrocarbon.

5. The method of claim 4 wherein said first fluid is a brine and said second fluid is oil.

6. The method of claim 4 wherein said first fluid is a brine and said second fluid is gas.

7. The method of claim 4 wherein said first membrane is hydrophobic and said second membrane is hydrophilic.

8. A method for conducting capillary pressure drainage and imbibition on a core sample of a porous rock, comprising the steps of:
    a) saturating a core sample of a porous rock with water,
    b) conducting a capillary pressure drainage cycle by injecting a hydrocarbon under pressure through a hydrophobic membrane into said core sample to displace the water from the core sample through a hydrophilic membrane,
    c) repeating step (b) during a plurality of additional capillary pressurized drainage cycles by successively increasing the pressure on the injected hydrocarbon,
    d) measuring capillary pressure versus saturation for each capillary pressure drainage cycle,
    e) conducting a first plurality of capillary pressure imbibition cycles by successively reducing the pressure on the injected hydrocarbon below the displacement pressure of the hydrophilic membrane to cause the displaced water to imbibe back into the core sample,
    f) conducting a second plurality of capillary pressure imbibition cycles by successively increasing pressure on the displaced water above atmospheric pressure as it imbibes back into the core sample, and
    g) measuring capillary pressure versus saturation for each capillary pressure imbibition cycle.

9. The method of claim 8 wherein each capillary pressure drainage and imbibition cycle is conducted after a state of fluid equilibrium has been reached within the core sample.

* * * * *